United States Patent [19]

Kiefer

[11] Patent Number: 5,648,613

[45] Date of Patent: Jul. 15, 1997

[54] SCAN ASSEMBLY AND METHOD FOR SIGNAL DISCRIMINATION

[75] Inventor: Karl F. Kiefer, Woodlands, Tex.

[73] Assignee: Gas Research Institute, Chicago, Ill.

[21] Appl. No.: 497,901

[22] Filed: Jul. 3, 1995

Related U.S. Application Data

[63] Continuation-in-part of Ser. No. 222,621, Apr. 5, 1994.

[51] Int. Cl.[6] .......................... G01N 29/06; G01N 29/10
[52] U.S. Cl. ................... 73/611; 73/623; 73/609
[58] Field of Search .................. 73/597, 602, 609, 73/610, 611, 612, 613, 614, 620, 622, 623, 625, 627, 629, 631, 634, 638; 364/507, 508

[56] References Cited

U.S. PATENT DOCUMENTS

| | | | |
|---|---|---|---|
| 2,723,357 | 11/1955 | Valkenburg et al. | 310/8.7 |
| 3,435,405 | 3/1969 | Persson . | |
| 3,435,406 | 3/1969 | McCauley . | |
| 3,482,434 | 12/1969 | Cowan et al. | 73/609 |
| 3,646,805 | 3/1972 | Walters . | |
| 3,714,816 | 2/1973 | Miller | 73/71.5 |
| 3,763,694 | 10/1973 | Rathburn et al. | 73/71.5 |
| 4,055,990 | 11/1977 | Topping | 73/623 |
| 4,131,018 | 12/1978 | Muller et al. | 73/432 |
| 4,170,143 | 10/1979 | Ries et al. | 73/609 |
| 4,198,866 | 4/1980 | Birjukov et al. | 73/613 |
| 4,285,243 | 8/1981 | Collingwood | 73/623 |
| 4,289,025 | 9/1981 | Norel et al. | 73/152 |
| 4,302,976 | 12/1981 | Bull | 73/639 |
| 4,304,134 | 12/1981 | Rouse et al. | 73/634 |
| 4,506,549 | 3/1985 | Thome | 73/582 |
| 4,513,621 | 4/1985 | Reinz et al. | 73/631 |
| 4,581,937 | 4/1986 | Lang et al. | 73/611 |
| 4,615,218 | 10/1986 | Pagano | 73/639 |
| 4,621,532 | 11/1986 | Takagi et al. | 73/623 |
| 4,691,572 | 9/1987 | van den Berg et al. | 73/643 |
| 4,718,277 | 1/1988 | Glascock | 73/622 |
| 4,735,087 | 4/1988 | Homrani et al. | 73/597 |
| 4,769,598 | 9/1988 | Krieg et al. | 324/219 |
| 5,007,291 | 4/1991 | Walters et al. | 73/640 |
| 5,014,711 | 5/1991 | Nagasaki | 128/660.07 |
| 5,046,033 | 9/1991 | Andreasen et al. | 364/580 |
| 5,170,346 | 12/1992 | Crawford et al. | 364/413.16 |
| 5,204,622 | 4/1993 | McCaslin et al. | 324/220 |
| 5,254,944 | 10/1993 | Holmes et al. | 324/220 |

*Primary Examiner*—Hezron E. Williams
*Assistant Examiner*—Rose M. Miller
*Attorney, Agent, or Firm*—Thomas, Kadyen, Horstemeyer & Risley

[57] ABSTRACT

A method and apparatus for discriminating a valid return pulse from noise in a return signal received by an ultrasonic transducer in response to an interrogating pulse transmitted into a wall of a gas pipe by an ultrasonic transducer of a scan assembly. A discriminator is provided to compare the return signal with adjustable reference voltage thresholds which are continually adjusted by a discriminator computer in accordance with the noise characteristics of the return signal.

11 Claims, 8 Drawing Sheets

5,648,613

SCAN ASSEMBLY AND METHOD FOR SIGNAL DISCRIMINATION

The present patent application is a Continuation-In-Part application of a co-pending patent application entitled "Scan Assembly Structure", filed on Apr. 5, 1994, and assigned Ser. No. 08/222,621.

FIELD OF THE INVENTION

The present invention relates generally to the inspection of buried natural gas pipes, and more particularly, to a scan assembly and method for the discrimination of data signals received by an ultrasonic transducer of the scan assembly.

BACKGROUND OF THE INVENTION

Thousands of miles of buried natural gas pipes of varying size and formed from various materials are presently in service. All of these mains are in some state of progressive degradation. In most instances, the extent of such degradation is unknown, and hence, the serviceability of the mains is similarly unknown. This lack of information with the respect to the degree of degradation results in unforeseen gas pipe leaks and/or breaks, and necessitates the expending of substantial time and expense in locating these defects so that repairs and/or replacement can be made. Because of the need to detect conditions which might result in gas pipe breaks and/or leaks, an apparatus has been developed for inspecting gas pipes, and such apparatus is usually referred to as a pipe line "pig" or "mouse." For purposes of clarity, such inspection apparatuses are referred to hereinafter as scan assemblies. Pipe line scan assemblies typically include a housing with a plurality of sensors, such as ultrasonic transducers, mounted to the outer surface thereof in a predetermined configuration or array to contact the inner surface of the gas pipe.

As a scan assembly advances axially down a gas pipe, the ultrasonic transducer associated therewith produces interrogation pulses which pass through a coupling medium and then intercept the surfaces defining both the inner diameter and the outer diameter of the gas pipe and any imperfections or flaws within the wall of the gas pipe. The surfaces defining the inner diameter and the outer diameter of the gas pipe and any imperfections or flaws within the wall of the pipe, in turn, cause the individual return pulses to be transmitted back to the ultrasonic transducer. By knowing the speed of sound in the different mediums through which the interrogation pulse travels (i.e., the coupling medium between the ultrasonic transducer and the pipe wall and the pipe wall itself), the thickness of the pipe wall can be computed by timing the difference between the return pulse from the inside surface of the pipe wall and the return pulse from the imperfection, flaw or outside surface of the pipe wall. A more thorough discussion of these principles is found in U.S. patent application Ser. No. 08/222,621, filed on Apr. 5, 1994, and entitled "Scan Assembly Structure", the disclosure of which is incorporated herein by reference.

It is well known in the industry to utilize ultrasonic transducers as sensors for inspecting gas pipes in the manner described above. Ultrasonic transducers typically comprise a ceramic disk fitted with two electrodes, one on the top surface and one on the opposite or bottom surface of the ceramic disk. When a voltage pulse is placed across the ceramic disk, it momentarily deforms into a dome shape. Since the deformation process is very fast, the change in mechanical shape works on the air or any other medium in contact with the ceramic disk. This work is absorbed by the adjacent medium as a mechanical vibration or pulse, thus the named transducer. This is a description of the transmit mode of a transducer whereby electrical energy is transformed into mechanical energy referred to as an interrogating pulse.

As mechanical energy, the pulse created is sent through the test material to be reflected from a target of interest, for instance, a surface defining a pipe wall or an imperfection in the pipe wall. Since time is used to calculate the thickness (i.e., the distance traveled to the target and back to the transducer), the target location and the target shape, there must be means for timing the "time of flight" of the pulse. This is typically accomplished by range gating in which a counter begins counting at the moment the interrogating pulse is generated, and at some later point in time when the return pulse is expected to be received, the system begins looking for the return pulse signal that represents a reflective pulse from the surface defining a pipe wall or an imperfection. The remaining data is gated out because it is assumed that no viable return pulse could return outside of the window of time in which the system is looking for the return pulse.

In the receive mode of an ultrasonic transducer, the transducer receives small return pulses in the form of mechanical vibrations that result from the interrogating pulse reflecting off the target of interest. However, only a small portion of the mechanical vibrations placed into the test material as an interrogating pulse by the ultrasonic transducer are reflected back to the ceramic disk by the target. The return pulses are coupled from the test material to the ultrasonic transducer by the same physical coupling material that was used to connect the transmitted interrogating pulse from the ceramic disk to the test material. When the mechanical vibrations hit the ultrasonic transducer, they cause a minute deformation in the ceramic disk. This changes the electrical characteristics of the ceramic disk which is detected, amplified, and filtered to produce an indication of the timing and amplitude of the return pulse. These return pulse properties can be related to the position of the target and its size by knowing the speed of sound through the test material and the energy attenuation characteristics of the test material.

Presently, the received return signals are compared with a predefined detection threshold for determining what is actually a return pulse and what is merely noise. This method has proven problematic due to the dynamic range of valid return signals. For example, a return pulse from the back wall of a gas pipe may be very strong for several interrogating pulses and then be very weak for several more. In a cast iron pipe, this could be the result of surface irregularities that scatter the input energy resulting in a weaker return pulse signal. Nonetheless, the return pulse from the back wall is equally valid in each case, and thus, must be reported as simply a "back wall." If the detection thresholds are set too high, the weak return pulses are ignored and the system would incorrectly report a very thin pipe wall at that point based upon the fact that it did not "see" a back wall. In addition, the amount of noise in the received return signal may vary over time during a scan, which if not corrected, will result in a false signal incorrectly positioning the back wall of the gas pipe. There are also circumstances under which the threshold level should be calibrated to the condition and/or material comprising the gas pipe being tested.

In view of the foregoing, it would be desirable to develop a method and apparatus for discriminating between actual data signals and noise, whereby the accuracy and reliability of the inspection is improved.

SUMMARY OF THE INVENTION

An object of the present invention is to overcome the deficiencies and inadequacies in the prior art as described above and as generally known in the industry.

Another object of the present invention is to improve the ability of a downhole scan assembly used in the inspection of gas pipes to discriminate between actual data received and noise in a dynamic fashion based upon the characteristics of the received signal.

Another object of the present invention is to provide signal discrimination means which consumes very little power in operation.

Briefly stated, the present invention is a scan assembly and apparatus for discriminating a valid return pulse from noise in a return signal received by an ultrasonic transducer in response to an interrogating pulse transmitted into a wall of a gas pipe by an ultrasonic transducer for inspecting a downhole gas pipes. The discriminator comprises a plurality of comparators which compare the return signal with adjustable detection thresholds set by digital-to-analog converters that are controlled by a discriminator computer. The quantized output of the comparators is temporarily stored in memory then downloaded into the discrimination computer for analysis. Based upon the analysis performed by the discrimination computer, the detection thresholds are adjusted in order to compensate for the noise characteristics of the pulse signal.

In addition to achieving all of the aforementioned objects, the present invention has numerous other advantages, a few of which are delineated hereafter as examples.

An advantage of a discriminator in accordance with the present invention is that it consumes very little power in operation, making it compatible for use in battery powered scan assemblies.

Another advantage of a discriminator in accordance with the present invention is that it is compact in size so as to readily fit within a scan assembly.

Another advantage of a discriminator in accordance with the present invention is that it allows return pulse signals, which would not otherwise be detected, to be detected as valid return pulses.

Other objects, features, and advantages of the present invention will become apparent from the following description when considered in conjunction with the accompanying drawings. All such additional objects, features, and advantages are intended to be included herein.

BRIEF DESCRIPTION OF THE DRAWINGS

The present invention, as defined in the claims, can be better understood with reference to the following drawings. The drawings are not necessarily to scale, emphasis instead being placed upon clearly illustrating the principles of the invention. Moreover, like reference numerals designate corresponding parts throughout the several views.

DETAILED DESCRIPTION OF THE PREFERRED EMBODIMENT

Figure 1:
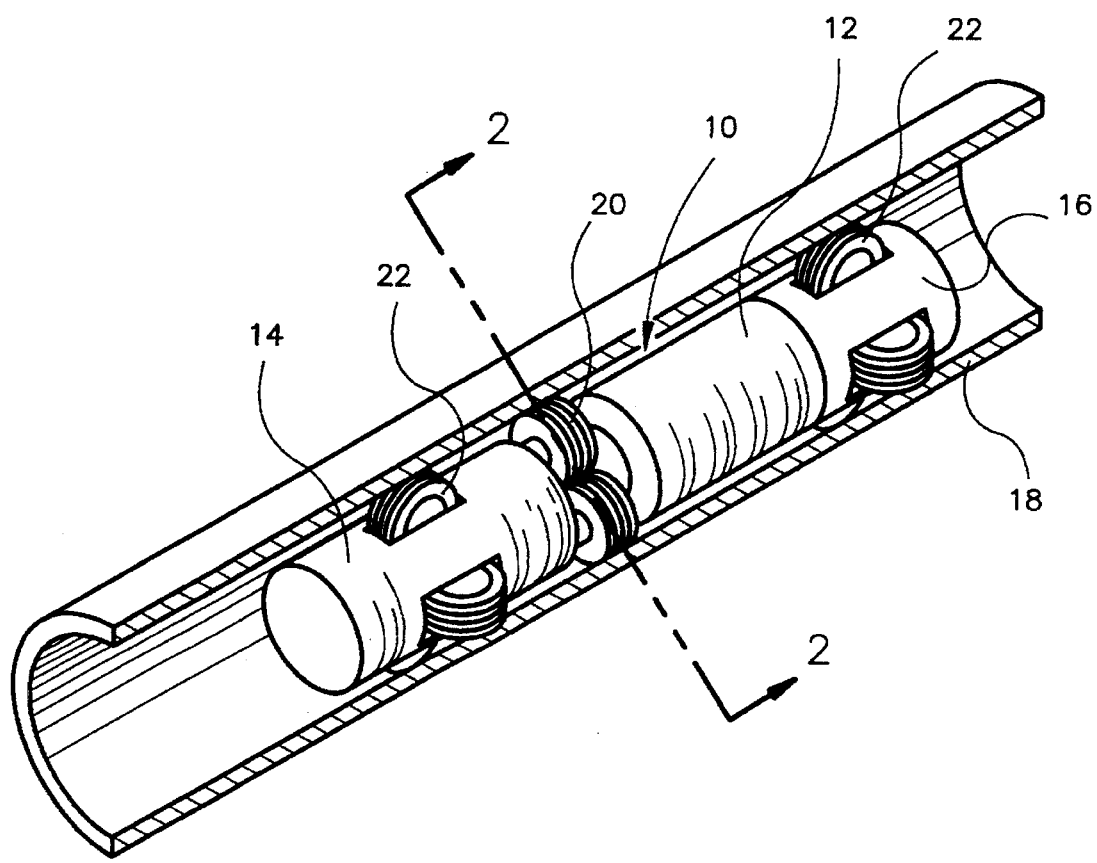
FIG. 1 is a perspective view, partially cut-away in cross-section, of a scan assembly.

Referring now to the drawings where the illustrations are for the purpose of describing the preferred embodiment of the present invention and are not intended to limit the invention described herein, FIG. 1 is a perspective view of a scan assembly 10 that can be utilized to transmit ultrasonic interrogating pulses into an object whose material is to be inspected and to receive return pulses from imperfections, flaws, or occlusions within the material or from surfaces thereon. The scan assembly 10 includes a sensor section 12 interposed between a front section 14 at one end of the scan assembly 10 and a rear section 16 at the other end thereof. The scan assembly 10 is receivable within the object to be inspected, such a gas pipe 18, and is moveable along the longitudinal axis of the gas pipe 18. The sensor section 12 includes a pair scan rollers 20 which are angularly positioned approximately 180 degrees relative to one another and canted slightly in the direction of travel of the scan assembly 10 through the gas pipe 18 so as to drive the scan assembly 10 therethrough. The canting or offsetting of the scan rollers 20 causes the scan assembly 10 to pull itself through the gas pipe 18 as the scan rollers 20 rotate. The front section 14 and the rear section 16 of the scan assembly 10 are provided with wheels 22 which are angularly positioned approximately 90 degrees relative to one another in each section 14, 16, and are oriented along the longitudinal axis of the assembly 10. The wheels 22 are coupled to rotation position sensors (not shown) so that axial movement of the scan assembly 10 within the gas pipe 18 and the location of the scan assembly 10 therein can be accurately monitored. A biasing mechanism (not shown, e.g., a spring) is provided and applies a radially outwardly directed force to each of the wheels 22, permitting the scan assembly 10 to be used within gas pipes 18 of various inner diameters.

Figure 2:
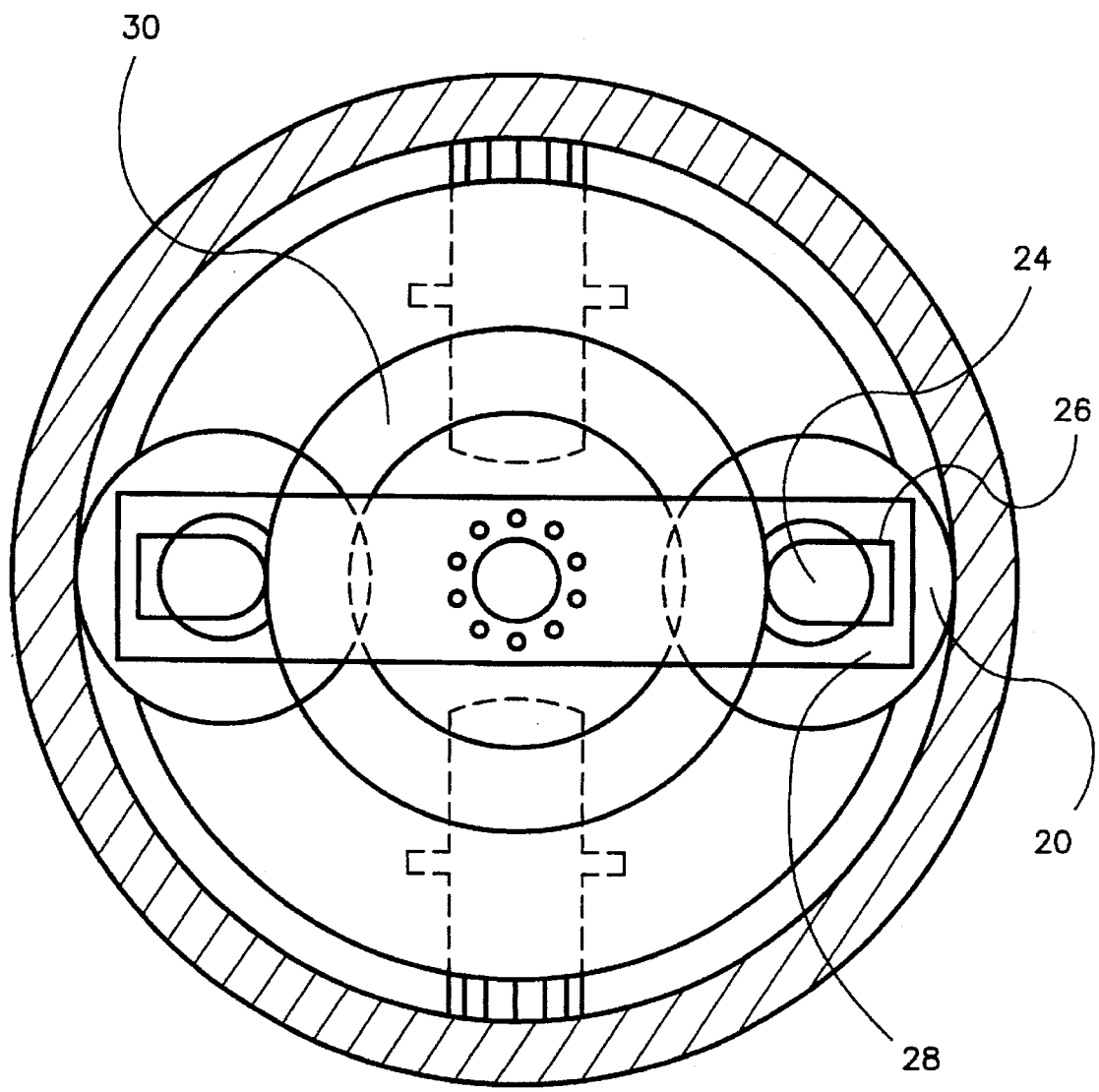
FIG. 2 is a partial cross-sectional view of the scan assembly of FIG. 1 taken substantially along lines 2—2 in FIG. 1.

Referring now to FIG. 2, an axle 24 about which a scan roller 20 rotates is received within an elongated slot 26 provided in either end of a crank arm 28 which is rotated by a scan motor 30 located within front section 14 of scan assembly 10. The elongated slot 26 permits radial movement of the scan roller 20 therein. A biasing mechanism (not shown; e.g., a spring), is provided and applies a radially outwardly directed force to the axle 24 of the scan roller 20 causing the scan roller 20 to grippingly engage the surface defining the inner diameter of the wall of the gas pipe 18. Rotation of the crank arm 28 via the scan motor 30 causes the scan roller 20 at either end thereof to similarly rotate resulting in the scan assembly 10 being propelled by the scan rollers 20 in an axial direction down the gas pipe 18. In addition, the rotation of the sensor section 12 as the scan assembly 10 moves axially down the gas pipe 18 produces a helical scan pattern of the wall of the gas pipe 18. This makes possible complete inspection of gas pipe 18.

Figure 3:
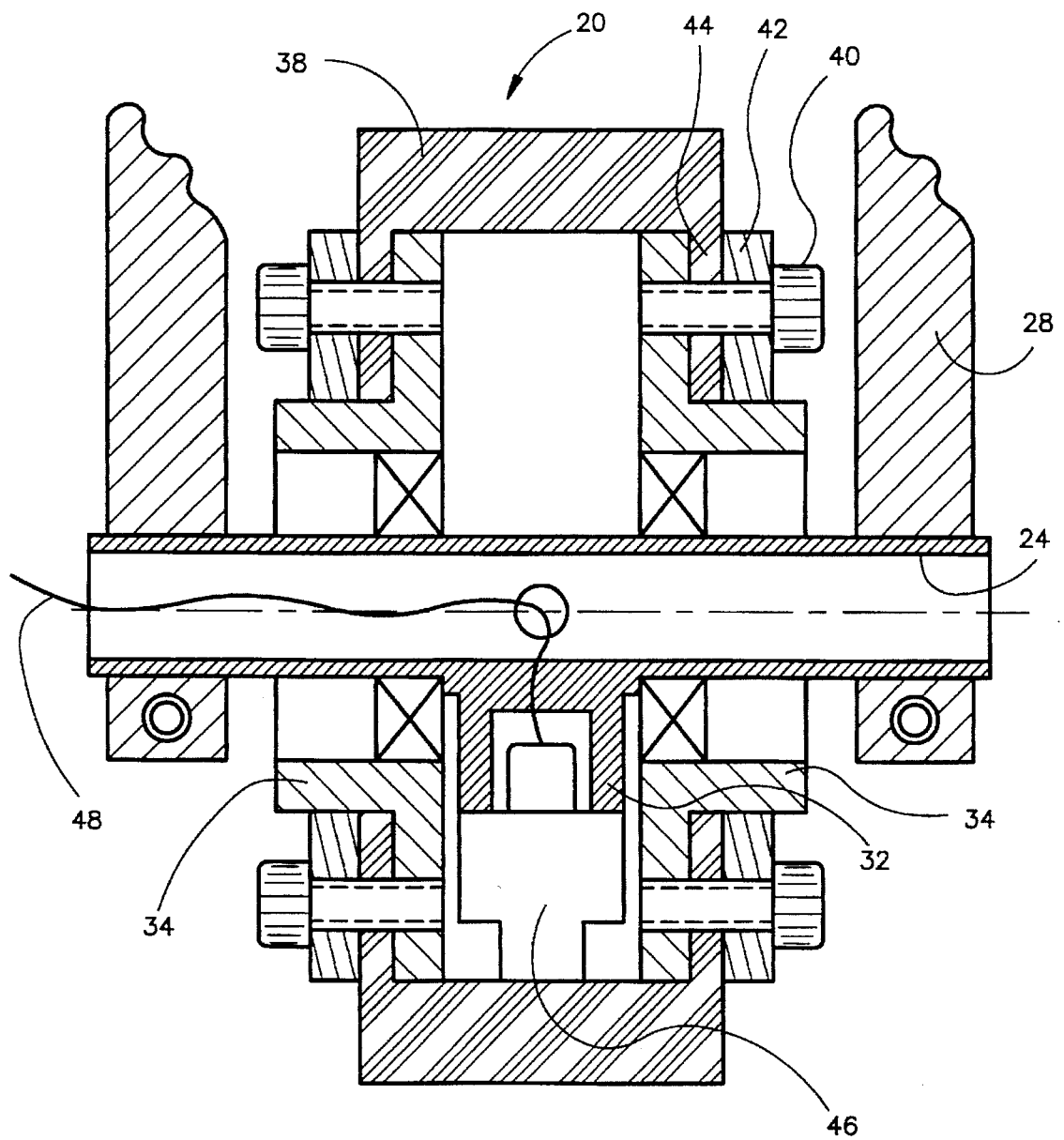
FIG. 3 is a cross-sectional view of the scan roller of the scan assembly of FIG. 1.

Referring now to FIG. 3, a cross-sectional view of a scan roller 20 rotationally mounted to the axial 24 is illustrated. A scan roller includes a hub 32 through which the axial 24 is received and attached thereto, a pair a spaced-apart side plates 34 between which the hub 32 is interposed, a pair of sealed bearings 36 for rotational mounting of the side plates 34 to the axial 24 and the hub 32, and a polymer tire 38 attached to the side plates 34 by fasteners 40 which are received through both a backing plate 42 and an inwardly directed lip of the tire 38 and which threadily engages a side plate 34. An ultrasonic transducer 46 is received within the scan roller 20 and is attached to the hub 32 therein. An electrical conductor 48 is connected to the ultrasonic transducer 46 and passes through the axial 24 permitting actuation of the transducer 46 resulting in the production of interrogating ultrasonic pulses which are transmitted through the wall of the tire 38, the coupling medium, into the wall of the gas pipe 18. Likewise, the receipt of return pulses from any interfaces encountered by the interrogating pulses are transmitted back through the wall of tire 38 to the ultrasonic transducer 46. Such interfaces, include but are limited to, the surface defining the inner diameter of the wall of the gas pipe 18, the surface defining the outer wall of the gas pipe 18, and any imperfections and/or flaws within the walls of the gas pipe 18.

The operation scan assembly 10 is based upon several principles or definitions. For instance, a shot is defined as an interrogating pulse produced by the ultrasonic transducer 46 that is directed into the wall of the gas pipe 18 to create return pulses that are used by the system to form tomographic images for diagnostic purposes of evaluating the condition of the gas pipe 18. The present scan assembly utilizes one or more shots, i.e., one or more interrogating pulses, per degree of radial rotation of crank arm 28 of sensor section 12. The return pulses permit the determination of the following: (1) radius of the inner diameter of the gas pipe 18 at the location where the return pulse is received; (2) radius of the outer diameter of the gas pipe 18 at the location where the return pulse is received; and (3) the location of the imperfections and/or flaws in the wall of the gas pipe 18 at the location where the return pulse is received.

Figure 4:
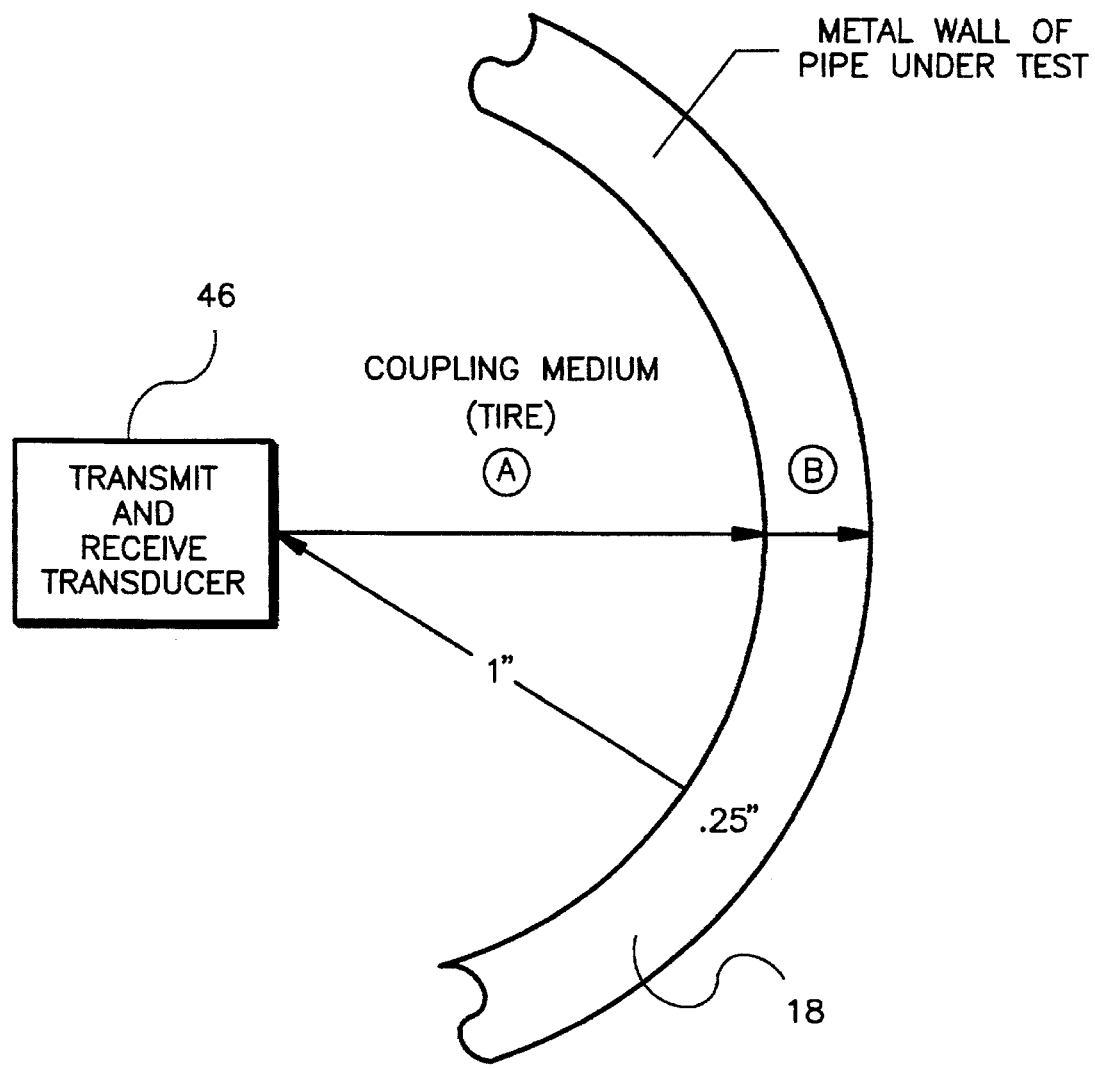
FIG. 4 is a schematic illustration of the relationship between the transducer and tire of FIG. 3 and the wall of the gas pipe.

Referring now to FIG. 4, the relationship between the ultrasonic transducer 46 utilized by the scan assembly 10 and the wall of the gas pipe 18 is illustrated. In this figure, area A represents the inside of the tire 38, that is, the coupling medium, in which the speed of sound is known and compensated for with respective temperature. The speed of sound in area A is nominally 4,000 feet per second which relates to 0.048 inches per microsecond. Area B represents the wall of the gas pipe 18 being inspected, which is cast iron for purposes of this illustration. The speed of sound in area B is 16,400 feet per second or 0.1968 inches per microsecond. By measuring the lapse time between the initiation of an interrogating pulse to the reception of a return pulse from a surface of gas pipe 18, various perimeters regarding the wall of the gas pipe 18 can be determined. For example, to determine the outer diameter of the gas pipe 18, the lapse time will be approximately twice the sum of the distance in areas A and B divided by the rate of sound travel in each area. For instance, 2.0 inches of travel in area A requires 41.66 seconds and 0.5 inches of travel in area B requires 2.54 microseconds. To determine the inner diameter of the gas pipe 18, the lapse time will be approximately twice the area A distance divided by the rate of sound travel in area A. Thus, since the travel of time in each area is known, the thickness of the wall of the gas pipe 18 can be computed from the lapse time between the return pulse from the surface defining the inner diameter of the gas pipe 18 and the return pulse from a surface defining the outer diameter of the gas pipe 18. Similar computations can be made to determine the location of any imperfections or flaws within the wall of the gas pipe 18. Therefore, the dimensions of the inner and outer diameter of the gas pipe 18, the thickness of the wall of the gas pipe 18, and the location of any imperfections or flaws within the wall of the gas pipe 18 can be readily determined through the use of the present scan assembly.

Figure 5:
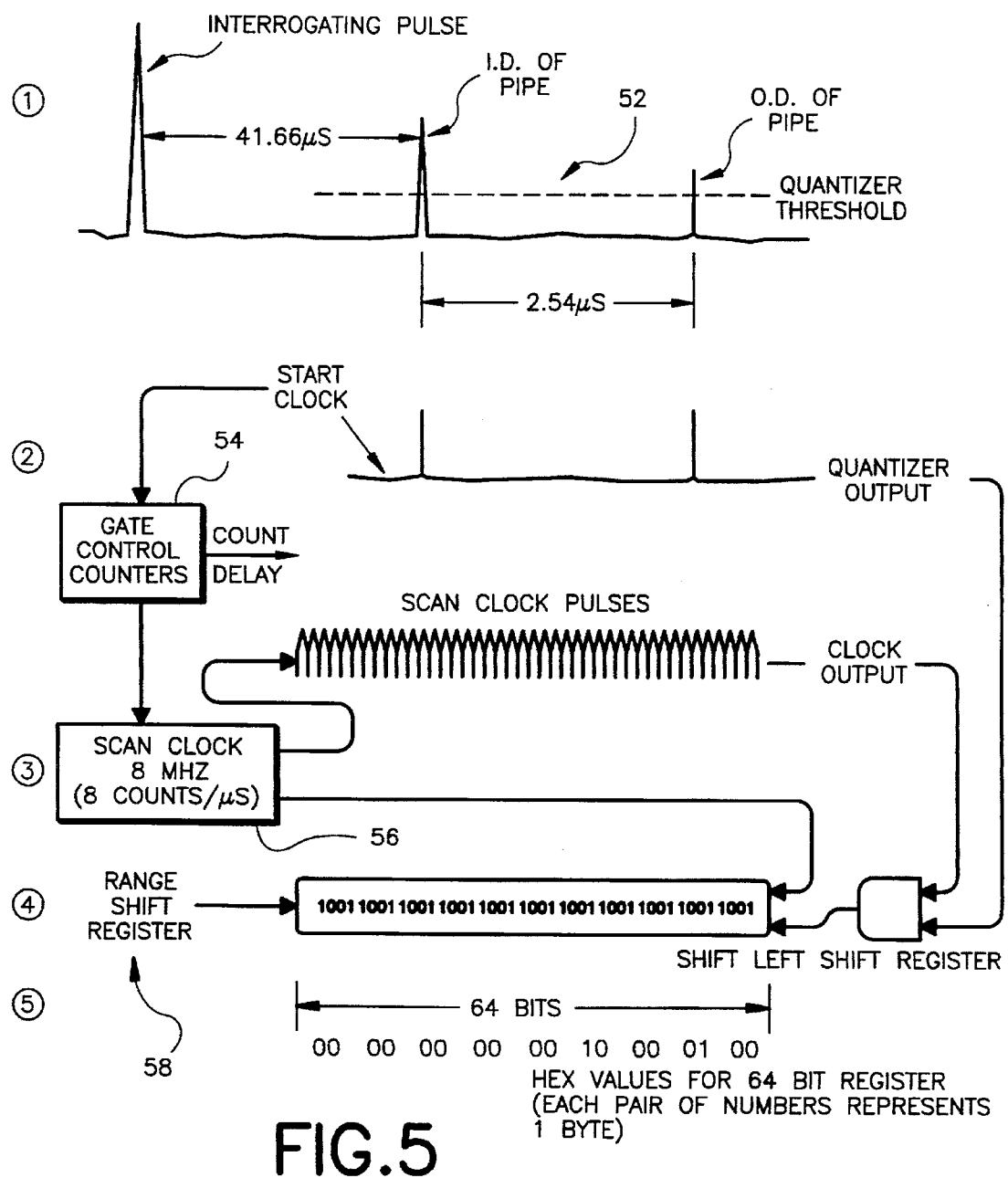
FIG. 5 is a timing diagram illustrating the gating function of the present invention.

Of critical importance to the operation of the present invention is the ability to recognize and/or detect the return pulses and to adequately measure the elapsed time between the return pulses attributal to the surface defining the inner diameter of the gas pipe 18 and the return pulses attributal to the surface defining the outer diameter of the gas pipe 18. A method by which this may be done is illustrated in FIG. 5, wherein the process of range gating is illustrated. Provided on line 1 is an illustration of the raw analog return data received by the ultrasonic transducer 46. These pulses represent a shot, i.e., an interrogating pulse, and the return pulses from the surfaces defining the inner and outer diameters of gas pipe 18. This line also shows the quantizer or detection threshold 52. Every time the threshold is exceeded, the quantizer (not shown) produces an output pulse as diagramed in line 2. Line 2 further shows the gate control counters 54. Gate control counters 54 are started at the time the shot is fired from the ultrasonic transducer 46 and record the lapse counts while the input signal is being ignored or gated out. When a preset delay count is reached, that is, the minimum amount of time for the return pulse from the surface defining the inner diameter of gas pipe 18 to arrive at transducer 46, the scan clock 56 is started and the logically combined scan clock pulses and quantizer output pulses are shifted into the range shift register 58, as diagramed on line 4. The range shift register 58 is a 64 bit register that can be serially loaded and then unloaded in parallel. Since the range data is serial in nature the register is loaded bit by bit as they come in from the scan clock 56. Once full, the entire shift register 58 is dumped in parallel to the I/O ports of the signal processor or scan computer (not shown), as diagramed on line 5. Hence, the only signal data sent to the signal processor or scan computer is that which is received within a specific window of time controlled by the gate control counters 54 and defined by the expected time of travel for viable return pulses.

In order to more efficiently and more accurately determine which signals received are noise and which are actually valid return pulses, the present invention provides a discriminator 60 which receives the raw return signal data from the transducer 46 and discriminates noise from valid signal data (e.g., return pulses from a pipe wall or imperfection). The discriminator 60 provides a means for high speed data comparison with a variable quantizer or detection threshold in a configuration which consumes very little power. The ability of the discriminator 60 to dynamically set the quantizer thresholds enables the scan assembly 10 to detect weak return pulse defining a pipe wall thickness which would otherwise not be detected and result in data "drop out."

In order for return signals received by the transducer 46 to be transferred to the discriminator 60 for discrimination, several things must occur. In this regard, please refer to FIG. 6 wherein the path of signal data is schematically illustrated. As shown, the return signals 61 are received by transducer 46 where their mechanical energy is converted to electrical energy as previously discussed. From transducer 46, the return signal is amplified and conditioned by transmitter/receiver 62. The transmitter/receiver 62 also controls the gain of each of the interrogating pulses produced by the transducer 46. The return signal is then transmitted across rotary transformer 64 which allows the transmission of signals across the rotating interface between rotating sensor section 12 and stationary end section 16. The return signal is then set to discriminator 60 for discrimination. Following discrimination, the return signal is further processed by digital signal processor 66 and scan control computer 68. Memory is provided to scan controller computer 68 in the form of RAM and ROM, generally denoted by reference numeral 72.

I. Discriminator Components

Figure 7:
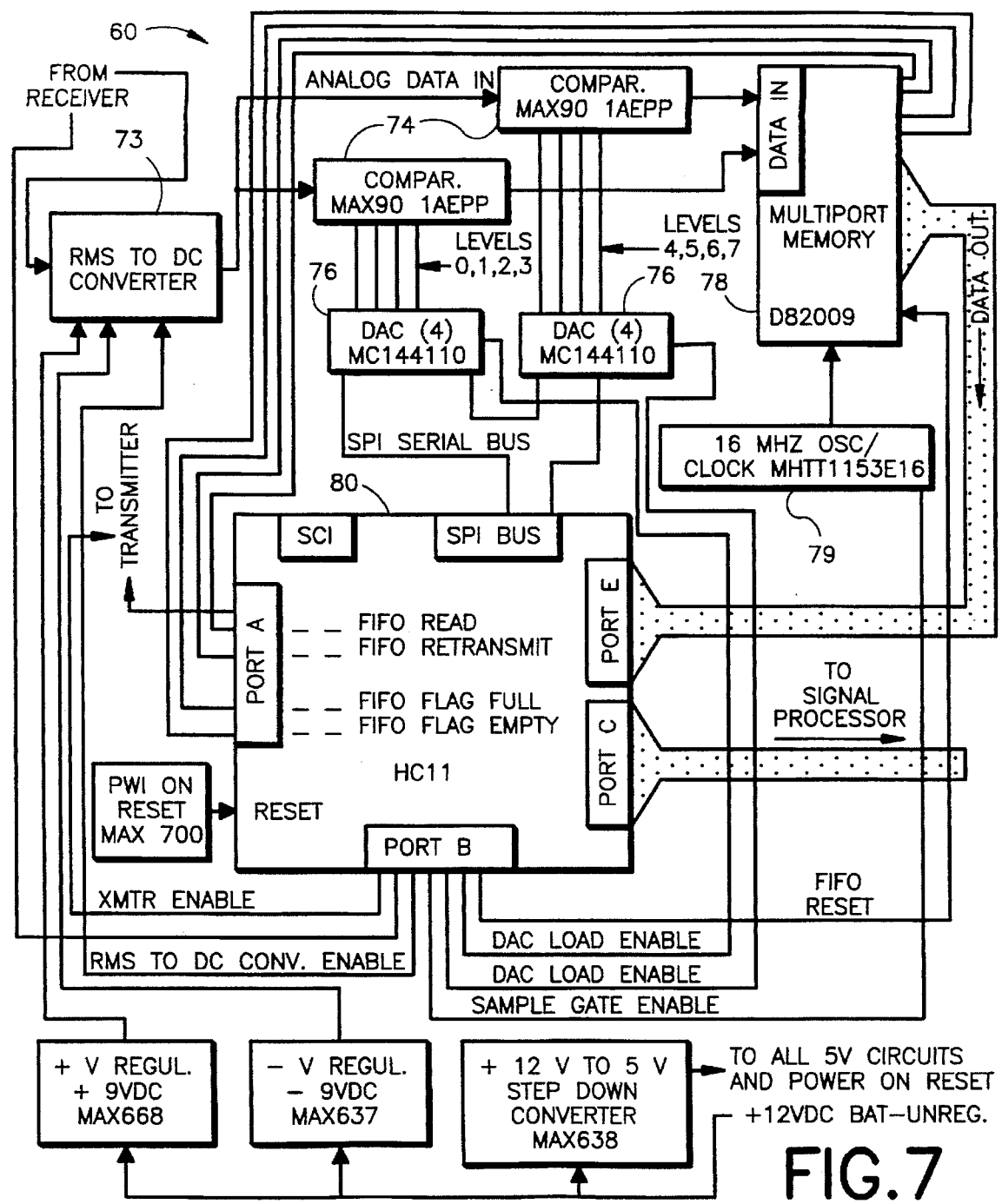
FIG. 7 is a schematic circuit diagram of a discriminator in accordance with the present invention.

To better understand discriminator 60, a schematic circuit diagram of a discriminator 60 in accordance with the present invention is illustrated in FIG. 7. Following is a brief discussion of the components of the discriminator 60 for purposes of discussing the preferred embodiment of discriminator 60 though it can be appreciated by one skilled in the art that a discriminator 60 in accordance with the present invention can take many forms and be comprised of other suitable components other than those discussed below.

First, provided is a root mean square (RMS) to direct current (DC) converter 73 which is a precision high speed rectifier/integrator that receives an AC coupled return signal and converts it to a DC value proportional to the RMS value of the alternating current (AC) waveform. In essence, this device captures all the energy from the return signal and presents without an AC component, in a form representing the energy of the received return signal.

Electrically connected to converter 73 are two parallel multiple input comparators 74 which are analog devices that output logic levels in response to the return signal value. Each multiple input comparator 74 in the preferred embodiment comprises four individual comparators, each individual comparator having a reference threshold voltage defined by the corresponding digital-to-analog converters (DAC) 76. The quantized output of the comparators 74 is determined by the relationship between the return signal value from the RMS-to-DC converter 73 and the multiple reference voltage thresholds defined by the DACs 76. When the return signal is below a particular reference voltage threshold, the output of that individual comparator of the multiple input comparator 74 is low. When the input pulse signal is higher than a particular reference voltage threshold, the output of that individual comparator of the multiple input comparator 74 is high. By changing the output of DACs 76 to comparators 74, the reference voltage thresholds are adjusted accordingly. The resulting output of comparators 74 is a quantized binary value of the return signal received by the discriminator 60.

A multi-port memory (MPM) 78 is provided as a buffer for temporary storage of the quantized data from the comparators 74. The MPM 78 comprises three states, the first of which is a working state where the MPM 78 is consuming considerable power but is doing an indispensable job of buffering and storing a high speed data stream from the comparators 74. The second state is not working but is on a standby and is ready to work when clocked by a 16 MHz sampling clock 79. Finally, the third state is the power down mode that is attained by a procedure of getting all the inputs to the chip in a high state. This is the state that is maintained during a waiting period between return signal data from consecutive interrogating pulses.

A discriminator computer 80 is provided as a central control device for the discriminator 60. The discriminator computer 80 can be any suitable microprocessor, such as an HC11 microprocessor. It is used as a simple "state" machine which executes the same control program over and over. In the present application, it is used in a single chip mode. That means no external memory is used for instructions or data. The primary purpose of the discriminator computer 80 is to continually evaluate the noise level of the received return pulse signal in order to dynamically set the reference voltage thresholds of the individual comparators of the multiple input comparators 74 by varying the code input to the DACs 76. In addition, the discriminator computer 80 controls the firing of interrogating pulses by the transducer 46 (FIG. 6), the conversion of data from the MPM 78 into a format for evaluation by the digital signal processor (DSP), and the coordination of all discrimination functions.

Further, discriminator computer 80 controls the gain of the return pulse signal via transmitter/receiver 62 (FIG. 6) and the independently adjustable detection voltage thresholds of comparators 74. The detection algorithms of discriminator computer 74 can therefore cause the power of the interrogating pulse to be varied to test the dynamic range of the return signals while using the same capability to maintain a constant false alarm rate that will ensure the detection of weaker valid return pulses. These changes to the detection process are done by control of the gain circuits on the transmitter/receiver 62 (FIG. 6) and reference voltage thresholds of the comparators 74. The discriminator computer 80 sets the quantizer thresholds by setting up the desired code input to the DACs 76. The DACs 76 output a voltage proportional to the input code from discriminator computer 80 and stable to the level of desired reference voltage threshold. The reference voltage thresholds are input to the multiple input comparators 74 so as to form multiple levels or thresholds of detection to which the return pulse signal from the receiver/transmitter 62 is compared. In the preferred embodiment, two input comparators 74, each having four comparators, are used resulting in eight levels of detection.

II. Discriminator Operation

The following description of the operation of the discriminator 60 is provided to assist in understanding the discrimination process. First, a return signal is received into discriminator 60 as analog information in the form of high frequency pulses. The analog pulse signal is converted to a DC value proportional to its RMS value by RMS-to-DC converter 73. This value is then inputted into multiple input comparators 74 where it is converted to quantized binary values by comparison to the reference voltage thresholds as set by the output of DACs 76, as previously discussed herein. At the instant in time that each sample of the return signal waveform is taken, each of the eight individual comparator thresholds of the two multiple input comparators 74 forms a bit input to an eight bit data word that will be the quantized value of the sample of the input pulse waveform. However, this quantized value is not to be construed as a straight analog-to-digital conversion of the input pulse waveform.

The reference voltage thresholds of the multiple input comparators 74 can be adjusted by the discriminator computer 80, thereby creating a nonlinear conversion. That is to say that the difference between each of the quantized thresholds may not be the same, but may be, for instance, logarithmic. The eight bit quantized value is then clocked into the MPM 78 for temporary storage at a sample rate that is sufficiently above the nyquist rate so as to match the transmitter/receiver 62 (FIG. 6) falter characteristics. In the preferred embodiment, the input rate of the comparators 74 is 16 MHz.

Of the return signal waveform received by the discriminator 60, only a small portion is converted by multiple input comparators 74 and stored in MPM 78. This is because the discriminator computer 80 has a finite capacity and speed, and therefore, is unable to receive data at the speed received by the discriminator 60. Further, a large percentage of the return signals received by the discriminator 60 are outside the gating envelope and need not be processed. For example, if a return signal were to be detected that indicated a back wall of the pipe at 25 cm and the pipe being surveyed was only 10 cm, then it is obvious that the return pulse was in error. There is no reason to test portions of the input waveform that are beyond a range of the pipe, and thus, the justification for range gating as described hereinbefore.

Figure 6:
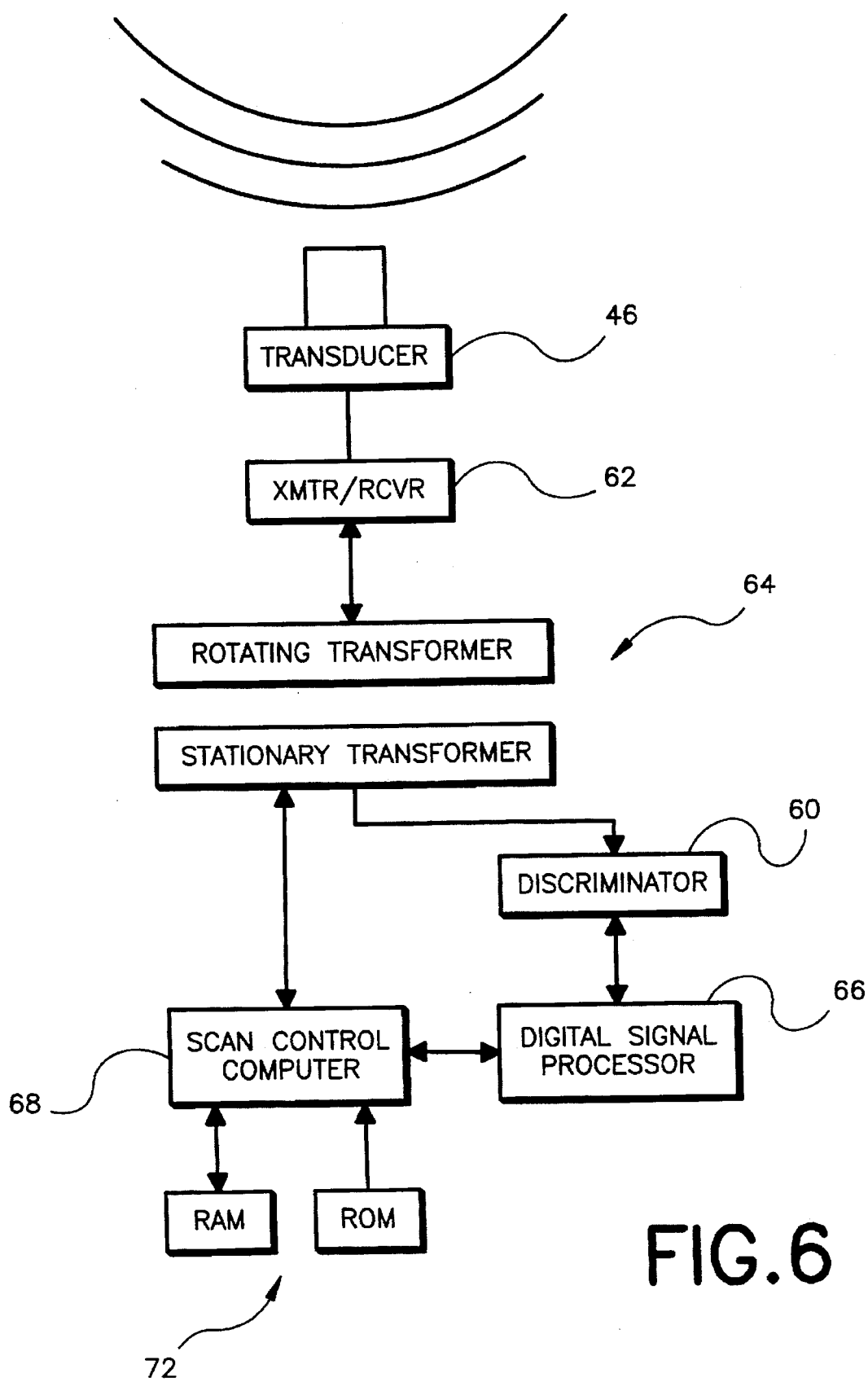
FIG. 6 is a schematic illustration of the signaling circuitry of the scan assembly of FIG. 1.

Once the return pulse waveform is converted by multiple input comparator 74 and stored in MPM 78, there is a delay until the next interrogating pulse returns to transducer 46 as a return pulse that is sent to the discriminator 60. During this delay, the discriminator computer 80 extracts the data from the MPM 78 at its own slower clock rate and processes this data for transmission to the digital signal processor 66 (FIG. 6). With the data from the MPM 78, the discriminator computer 80 evaluates the noise level and the actual return pulse level so as to optimize signal discrimination by dynamically adjusting various operating parameters such as, but not limited to, the reference threshold voltages provided to the multiple input comparators, the level of the interrogating pulse, and the gain of the return signal. By the time the data from the next interrogating pulse is due, the discriminator computer 80 is finished processing and is ready to receive another burst of data from the MPM 78. This discrimination process is repeated for each return signal received by the discriminator 60.

III. Return Pattern Detection Process

In addition to the aforementioned discrimination process utilizing a "one shot" interrogating pulse which is transmitted into the test pipe wall, the return pulses or reflections of which are measured in time displacement to determine the presence of a back wall or a flaw in the test pipe walls, a discriminator 60 in accordance with the present invention is capable of flaw detection using a near field energy return pattern process referred to hereinafter as return pattern detection. This process is not intended to replace the "one shot" process but is considered to supplement that approach. The pattern detection approach utilizes energy that had previously been described in the "one shot" approach. The energy utilized is the reflected and refracted portions of the interrogating pulses that are trapped in the material under test after the entry of the interrogating pulse. When the initial pulse enters a test material, it travels to the back wall and is reflected. The reflected pulse is the energy of the interrogating pulse minus this dispersion of the pulse in the material, the refraction of the imperfect surfaces of the back wall, and the losses that escape the back wall into the soil, air or whatever is adjacent to the outside diameter of the gas pipe 18.

The reflected pulses then proceeds back to the entry point and two things happen. Some of the pulse escapes the inside diameter of the gas pipe 18 into the couplet medium (e.g., tire 38) to the transducer 46 where it is received, and some of it is reflected back to the back wall of the gas pipe 18. This process, called reverberation, continues until all the energy of the interrogating pulse dissipated by the aforementioned mechanisms. The energy trapped by this process continues to reflect back and forth several times. The actual number of times is a measure of the amount of energy that coherently enters the gas pipe 18 from the transducer's interrogating pulse. The more energy that enters gas pipe 18, the longer the reverb pattern will be. This amount of coherent energy is a function of the quality of the entry surface, the flaws in the path of the pulse, and the quality of the reflecting surface. If any of these three parameters are less than perfect, the reverb pattern will be reduced in amplitude and time. This reduction would indicate the presence of one or more of a less than perfect surface condition or blockage of the reflected signal that can be interpreted as a flaw.

Figure 8A:
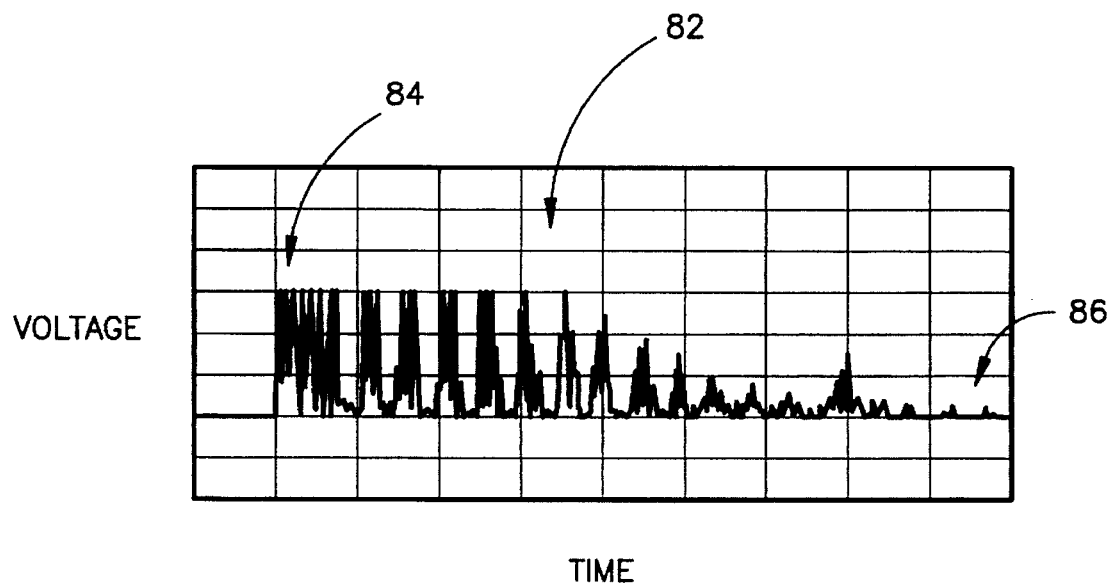
FIG. 8A is a graphical illustration of a reverberation pattern of for a pipe wall without an imperfection or flaw.

As an example, FIG. 8A illustrates an essentially perfect reverberation pattern 82 of trapped energy that is reflected from wall to wall within a gas pipe 18. The pattern 82 begins with an interrogating pulse 84 entering the material and ends at a position in the time when the reflection, refraction, conduction, and mechanical source impedance (related to bulk modules) of the system has dissipated all the energy, indicated generally by reference numeral 86.

Figure 8B:
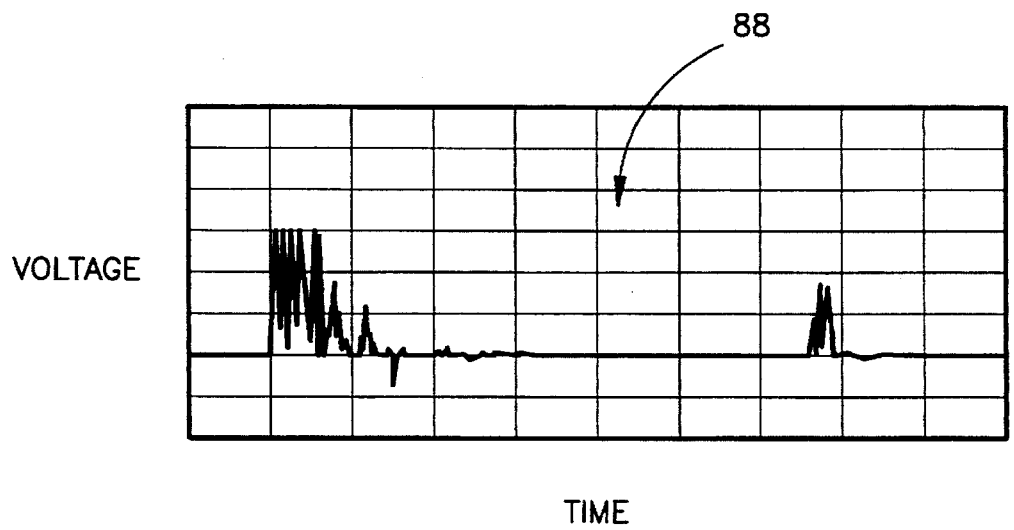
FIG. 8B is a graphical illustration of a reverberation pattern of for a pipe wall with an imperfection or flaw.

In comparison, FIG. 8B illustrates a reverberation pattern 88 from a pipe having a flaw. Detection in this case can be preformed visually by reference to the absence of reverberating pulses in the middle portion of pattern 88, though in practice such would be performed by the digital signal processor 66 (FIG. 6), scan control computer 68 (FIG. 6) and discriminator 60. Note, the dramatical reduction in the reverberation pattern 88 results from the energy of the initial pulse being scattered so that little or none remained as a coherent waveform that could continue to reverberate.

It is interesting to note that the materials in and around the inspected area of the gas pipe 18 can be viewed as a filter. When excited with an interrogating pulse, the filter rings out at a frequency and duration that is unique to the filter. Given another location on the pipe, it is highly likely that the characteristics of the filter would be different. This is a further avenue for flaw detection by means of constantly calculating a digital filter that is made up of coefficients that represent the nominal (i.e., no flaw) case of $$\frac{\sin x}{x}$$

energy decay. Incoming signal data would then be sent through the digital filter. Flaw areas would produce coefficient patterns that would not match the nominal case, and thus, the filter calculations would produce an unusually large error signal. Note, error signal production is inherent to the linear predictive filter calculation process. Therefore, fluctuations of the error signal can be used to detect flaws in the material under test.

The return pattern approach to detection offers other benefits for making available a wealth of signal processing techniques previously only applied to automated pattern recognition, video pattern detection, and synthetic aperture radar processes.

Moreover, it will be understood that the invention is not restricted to the particular embodiments described herein, and that many modifications can be made to such embodiments by one skilled in the art without departing from the spirit of the invention as defined by the following claims.

Wherefore, the following is claimed:

1. A scan assembly for inspecting a downhole gas pipe using an ultrasonic transducer to transmit interrogating pulses into a wall section of said downhole gas pipe and for receiving return signals which are analyzed for evaluating the condition of said downhole gas pipe, comprising:

a discriminator for discriminating between a valid return pulse and noise in the return signal received by said transducer, said discriminator comprising a plurality of comparators which compare the return signal with respective adjustable multiple reference voltage thresholds;

control means for dynamically adjusting said adjustable reference voltage thresholds of said comparators based on the amount of noise and the strength of said return signal; and analyzer means for analyzing the return signal for indication of an inner surface of said wall section and an outer surface of said wall section so as to indicate the pressure of an imperfection in said wall section.

2. The scan assembly of claim 1, wherein said reference voltage thresholds have a linear relationship of each other.

3. The scan assembly of claim 1, wherein said reference voltage thresholds have a non-linear relationship to each other.

4. The scan assembly of claim 1, wherein said discriminator produces a quantized output that is received by said analyzer.

5. The scan assembly of claim 1, wherein said control means dynamically adjusts the power level of said interrogating pulses based on the amount of noise and strength of said return signal.

6. A method for inspecting a downhole gas pipe in which an interrogating pulse is transmitted into a wall of said downhole gas pipe by an ultrasonic transducer and a return signal is received by said ultrasonic transducer, said method comprising the steps of:

transmitting an interrogating pulse with said transducer into said wall of said gas pipe;

receiving return signals with said transducer, said return signals comprising valid return pulse data and noise;

discriminating between said valid return pulse data and said noise within said return signals with a discriminator; and adjusting operation of said discriminator based on the amount of said noise and strength of said return signals;

analyzing said return signals for indications of an inner surface of said wall of said downhole gas pipe and an outer surface of said wall of said downhole gas pipe so as to indicate the presence of an imperfection in said wall of said downhole gas pipe.

7. The method of claim 6, wherein said step of discrimination comprises the steps of:

comparing said return signal with a plurality of adjustable reference voltage thresholds so as to quantized said return signal; and analyzing said quantized return signal in order to determine the appropriate value for said reference voltage thresholds.

8. The method of claim 7, wherein said return signal is constantly analyzed for determining the appropriate setting for said reference voltage thresholds.

9. The method of claim 7, wherein said return signal is rectified before being compared with said reference voltage thresholds.

10. A method for inspecting a downhole gas pipe in which an interrogating pulse is transmitted into a wall of said downhole gas pipe by an ultrasonic transducer and a return signal is received by said ultrasonic transducer, said method comprising the steps of:

transmitting an interrogating pulse with said transducer into said wall of said gas pipe;

receiving a return signal with said transducer, said return signal comprising valid return pulse data and noise;

discriminating between said valid return pulse data and said noise within said return signal with a discriminator; and analyzing said return signal for indications of an imperfection in said wall of said downhole gas pipe, wherein the step of analyzing includes the steps of monitoring a reverberation pattern of said return pulse and determining if an energy reduction appears in said reverberation pattern so as to indicate the presence of an imperfection in said wall of said gas pipe.

11. A method for discriminating a valid return pulse from noise in a return signal received by an ultrasonic transducer in response to an interrogating pulse transmitted into a wall of a gas pipe by an ultrasonic transducer for inspecting a downhole gas pipes, comprising the steps:

comparing said return signal with a plurality of adjustable reference thresholds so as to quantize said return signal;

analyzing said quantized return signal in order to determine the appropriate value for said reference thresholds based upon the level of said noise in said return signal; and adjusting said reference thresholds and power of said interrogating pulse in order to detect valid return pulse data.

\* \* \* \* \*